United States Patent

Shimashita et al.

[11] Patent Number: 5,822,034
[45] Date of Patent: Oct. 13, 1998

[54] OPHTHALMOLOGIC APPARATUS

[75] Inventors: Satoshi Shimashita, Tachikawa; Takashi Masuda, Yamato; Yoshimasa Hamano, Fuchu; Koji Uchida; Toshifumi Masaki, both of Utsunomiya, all of Japan

[73] Assignee: Canon Kabushiki Kaisha, Tokyo, Japan

[21] Appl. No.: 668,329

[22] Filed: Jun. 25, 1996

[30] Foreign Application Priority Data

Jun. 29, 1995 [JP] Japan .................................. 7-185020

[51] Int. Cl.⁶ .......................................................... A61B 3/10
[52] U.S. Cl. ............................................. 351/212; 351/205
[58] Field of Search ...................................... 351/211, 212, 351/247, 246, 205, 208, 200, 221; 128/652, 645, 648

[56] References Cited

U.S. PATENT DOCUMENTS 4,660,946 4/1987 Nakamura et al. .
4,666,269 5/1987 Nakamura et al. .
4,704,012 11/1987 Kohayakawa et al. .
4,710,003 12/1987 Masuda et al. .
4,755,041 7/1988 Ishikawa et al. .
4,764,006 8/1988 Hamano et al. .
4,894,670 1/1990 Masuda .
5,056,522 10/1991 Matsumura et al. .
5,107,851 4/1992 Yano et al. .
5,302,979 4/1994 Maeda et al. .
5,365,286 11/1994 Masuda .
5,500,696 3/1996 Masuda et al. .

Primary Examiner—Hung X. Dang
Attorney, Agent, or Firm—Fitzpatrick, Cella, Harper & Scinto

[57] ABSTRACT

This specification discloses an ophthalmologic apparatus for executing an eye examination on an eye to be examined. The ophthalmologic apparatus is provided with an eye examination unit, an alignment drive system for driving the eye examination unit to thereby execute the alignment between the eye examination unit and the eye to be examined, a time measuring portion, and a control system for causing the alignment drive system to drive the eye examination unit on the basis of the output of the time measuring portion so as to return the eye examination unit to an eye examination waiting position.

15 Claims, 8 Drawing Sheets

5,822,034

OPHTHALMOLOGIC APPARATUS

BACKGROUND OF THE INVENTION

1. Field of the Invention

This invention relates to an ophthalmologic apparatus for use in ophthalmologic clinics, opticians' stores, etc.

2. Related Background Art

In ophthalmologic apparatus according to the prior art, there are known an eye axis length meter for measuring an eye axis by an ultrasonic wave, an ophthalmotonometer, an eye refraction measuring meter, and the like, but when, for example, the eye axis length meter is left unoperated for a predetermined time, an ultrasonic probe for contacting with an eye to be examined and measuring the length of the eye axis moves in a direction opposite to a direction in which the eye to be examined is located during measurement and stops at a predetermined position. Thereby, when the next examinee is to be measured, the ultrasonic probe is prevented from contacting with the eye to be examined when the examinee's brow and chin contact with a brow applier and chin rest, respectively to fix the examinee's head. It is often the case that at the same time, the electricity saving function of saving electricity or extending the service life of each member works.

Also, when the ultrasonic probe has been changed from the ultrasonic probe disinfecting mode for disinfecting the tip end of the ultrasonic probe to the cornea shape measuring mode for measuring the refracting power, the radius of curvature, the degree of astigmatism, the angle of the astigmatic axis and the like of the cornea of the eye to be examined, the ultrasonic probe moves in a direction opposite from the eye to be examined and stops at a predetermined position and effects the measurement of the shape of the cornea. When the mode is thus changed before the measurement is started, the ultrasonic probe moves in the direction opposite from the eye to be examined.

Further, after the termination of the measurement, a switch is depressed, whereby a measuring portion moves to a predetermined position substantially at the center of the width of the examinee's left and right eyes and stops there, or when the measurement is to be resumed, the switch is depressed, whereby the measuring portion moves to a predetermined position near the examinee's left eye or right eye and stops there, and the measurement of the next examinee is done quickly.

In the above-described example of the prior art, however, when the ophthalmologic apparatus is not operated for a predetermined time, means for moving the tip end of an eye examining portion such as the ultrasonic probe in the direction opposite to the direction in which the eye to be examined is located is means discrete from means for aligning the eye examining portion with the eye to be examined, and this leads to a high cost and an economical burden.

Also, when the mode has been changed, the eye examining portion moves in the direction opposite from the eye to be examined, but when the eye examination of an examinee has been terminated and the next examinee is to be examined, there is not provided a switch for moving the eye examining portion to a predetermined position in a measurement waiting state so that the tip end of the eye examining portion can be prevented from contacting with the eye to be examined or the next eye examination can be done quickly. That is, there is no simple operating means for an examiner himself to move the eye examining portion to the predetermined position in the measurement waiting state. Further, this example of the prior art is not efficient for examining many examinee within a short time.

Particularly, there is not yet known any device for disposing the eye examining portion reliably in the waiting state at the end of the eye examination with respect to a direction opposed to the eye to be examined.

There is neither known a device for disposing the eye examining portion reliably in the waiting state when a power source has been cut off.

SUMMARY OF THE INVENTION

It is a first object of the present invention to provide an ophthalmologic apparatus in which the return to a waiting position conforming to time can be realized by more simple construction.

It is a second object of the present invention to provide an ophthalmologic apparatus which can be reliably returned to a waiting position with respect particularly to a direction opposed to an eye to be examined after the termination of an eye examination.

It is a third object of the present invention to provide an ophthalmologic apparatus which can be reliably returned to a waiting position when a power source has been cut off.

Other objects of the present invention will become apparent from the following detailed description of some embodiments of the invention.

DESCRIPTION OF THE PREFERRED EMBODIMENTS

Figure 1:
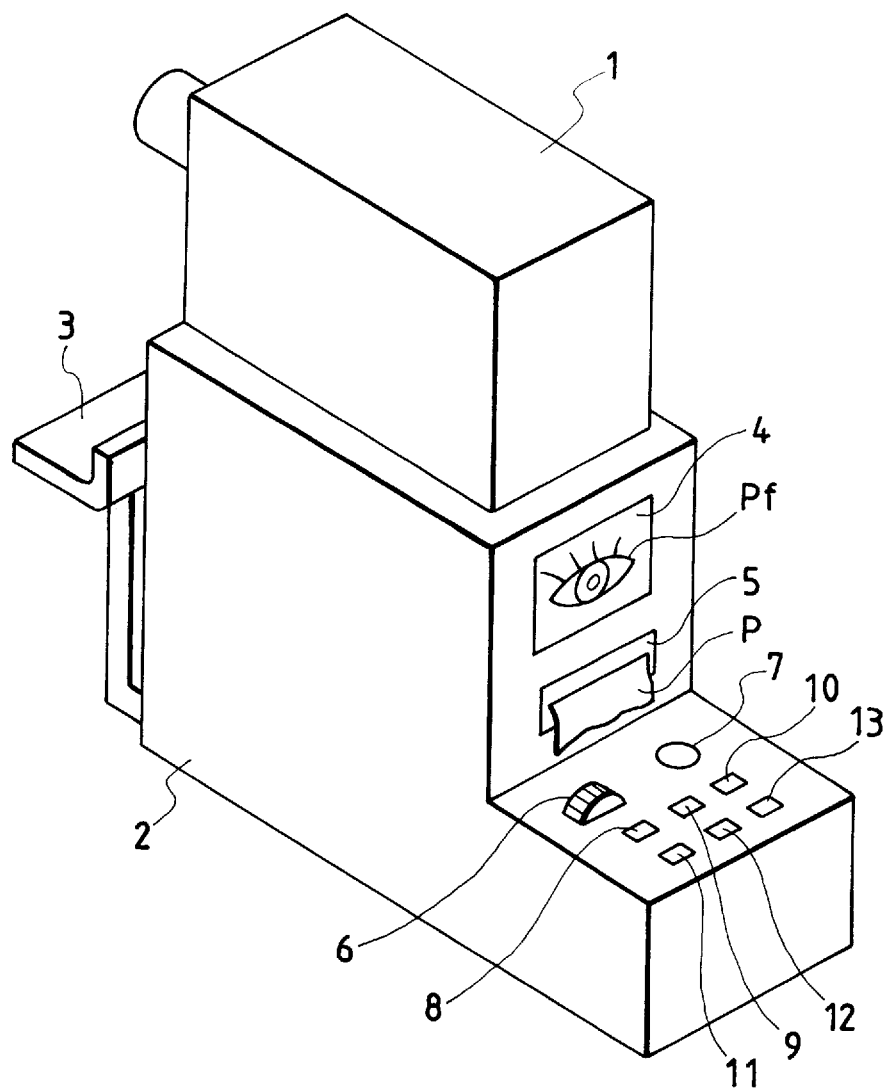
FIG. 1 is a perspective view of a first embodiment of the present invention.

The invention will be described in detail with respect to some embodiments thereof shown in the drawings.

FIG. 1 is a perspective view of an apparatus according to a first embodiment of the present invention which is an example of a non-contact type ophthalmotonometer. A measuring portion 1 for effecting an eye examination is movably placed on a fixed base 2, on which there are provided a chin rest 3 for fixing the position of an examinee's head and movable in a vertical direction, a liquid-crystal monitor 4 for displaying the image of an eye to be examined and a measured value, and a printer 5 for printing on printing paper P the results of the examination of the left and right eyes, the frequency of the eye examination, the date and time of the eye examination, the name of the examinee, ID number and the like.

Also, as the operating portion of the fixed base 2, there are provided a roller 6 for moving the measuring portion 1 in the forward and rearward direction which is an eye axis to thereby align it with the eye to be examined, a track ball 7 adapted to be rotated to thereby move the measuring portion 1 in vertical and horizontal directions and align the measuring portion 1 with the eye E to be examined, a print switch 8 for executing the printing of the printer 5, a power source switch 9 for turning on and off a power source, a chin rest raising switch 10 for raising a chin rest 3, a chin rest lowering switch 11 for lowering the chin rest 3, an eye examination switch 12 for effecting an eye examination, and a sleep switch 13 for moving the measuring portion 1 to a predetermined position and stopping the supply of electricity to each member to save electricity and extend the service life of each member.

Setting is done such that when the track ball 7 is rotated in the forward and rearward direction, the measuring portion 1 moves in a vertical direction relative to the examinee, and when the track ball 7 is rotated in the leftward and rightward direction, the measuring portion 1 moves in a horizontal direction relative to the examinee, and when the roller 6 is rotated in the forward and rearward direction, the measuring portion 1 moves in the forward and rearward direction relative to the examinee.

Figure 2:
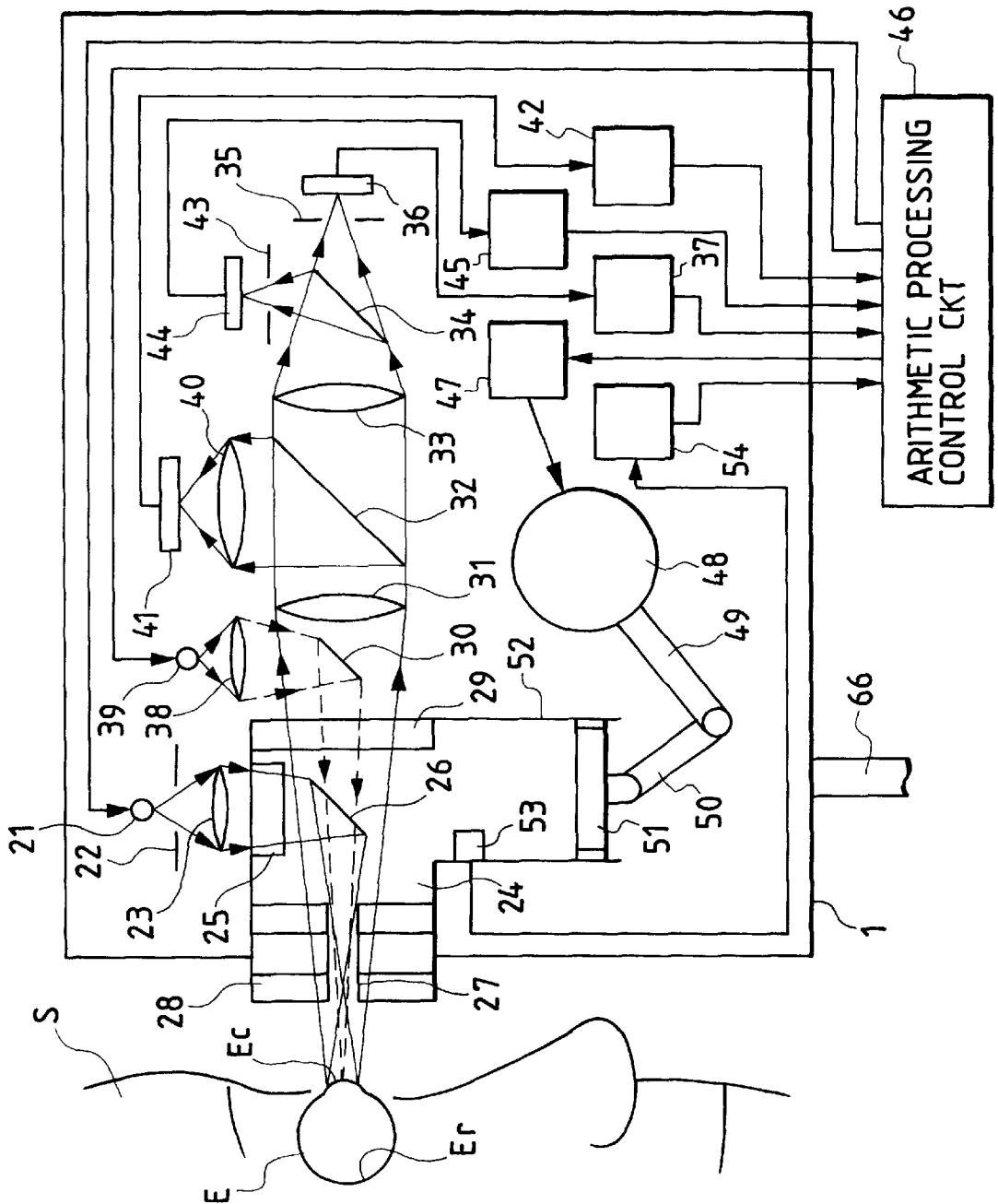
FIG. 2 shows the construction of an optical system and a circuit in a measuring portion.

FIG. 2 is a block circuit diagram of the interior of the measuring portion 1. On the optical path leading from a light source 21 for eye examination to the eye E to be examined, there are successively arranged an aperture 22, a lens 23, a light passing member 25 provided in a chamber 24, a light dividing member 26 in the chamber 24, and an apertured light passing member 28 provided with a nozzle 27 for blowing out air therethrough to the cornea Ec of the eye E to be examined.

On the optical path behind the light dividing member 26, there are successively arranged a light passing member 29 provided in the chamber 24, a light dividing member 30, a lens 31, a light dividing member 32, a lens 33, a light dividing member 34, an aperture 35 and a light receiving element 36, the output of which is connected to an alignment detection circuit 37 for detecting whether alignment is right or not.

Setting is done such that by the alignment between the eye E to be examined and the measuring portion 1, the focus of the convergent light on the aperture 35 is varied and the quantity of light incident on the light receiving element 36 is varied and when the quantity of light on the light receiving element 36 becomes maximum, the alignment between the eye E to be examined and the measuring portion 1 becomes right. An alignment light receiving portion is constituted by the aperture 35 and the light receiving element 36 so that the eye E to be examined and the tip end portion of the nozzle 27 can be brought into a positional relation capable of effecting an eye examination.

On the optical path in the direction of incidence of the light dividing member 30, there are arranged a lens 38 and a fixation lamp 39 for fixing the visual axis of the eye E to be examined. On the optical path in the direction of reflection of the light dividing member 32, there are arranged a lens 40 and a TV camera 41, the output of which is connected to an image signal processing circuit 42 for processing an image signal.

On the optical path in the direction of reflection of the light dividing member 34, there are arranged an aperture 43 and a light receiving element 44, the output of which is connected to a predetermined deformation detection circuit 45 for detecting whether the cornea Ec of the eye E to be examined has made predetermined deformation. The light receiving element 44 is set such that the quantity of light thereon becomes maximum when the cornea Ec makes the predetermined deformation, and the aperture 43 and the light receiving element 44 together constitute a deformation detection light receiving portion for effecting the predetermined deformation of the cornea Ec.

The outputs of the alignment detection circuit 37, the image signal processing circuit 42 and the predetermined deformation detection circuit 45 are connected to an arithmetic processing control circuit 46, the output of which in turn is connected to the light source 21 for eye examination and the fixation lamp 39. Further, the output of the arithmetic processing control circuit 46 is connected to a rotary solenoid drive circuit 47 in the measuring portion 1 so as to drive a rotary solenoid 48 by a drive signal from the rotary solenoid drive circuit 47. The rotation of the rotary solenoid 48 may be transmitted to a piston 51 by a link mechanisms 49 and 50 so that the piston 51 may be linearly moved in the chamber 24 by a cylinder 52.

Also, a pressure sensor 53 for detecting pressure is provided in the chamber 24, and the output of this pressure sensor 53 is connected to a pressure detection circuit 54 for receiving as an input a signal corresponding to the pressure thereof and finding the pressure in the chamber 24, and to the arithmetic processing control circuit 46.

Figure 3:
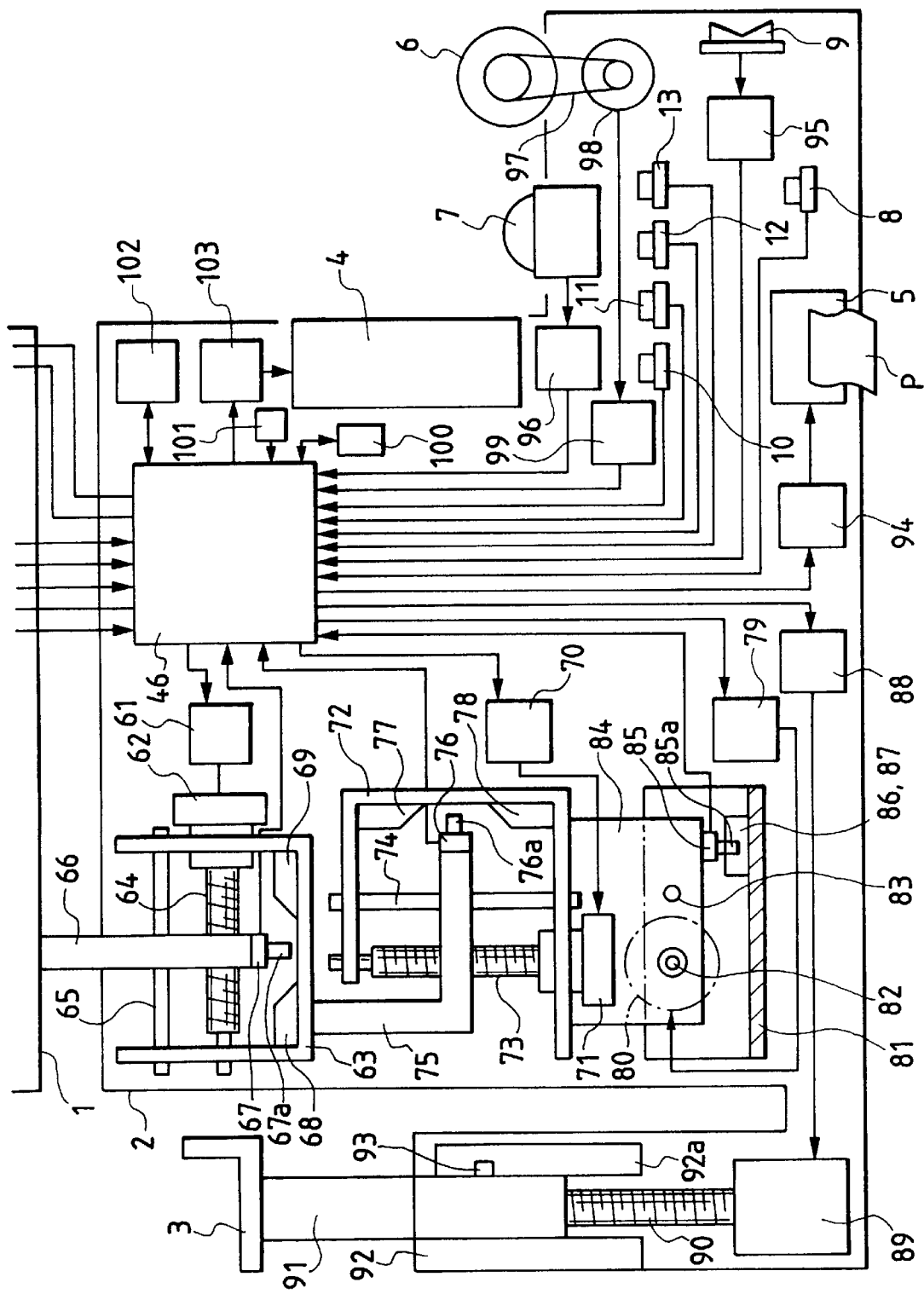
FIG. 3 is a block circuit diagram of the interior of a fixed base.

Referring now to FIG. 3 which is a block circuit diagram of the interior of the fixed base 2, the output of the arithmetic processing circuit 46 is connected to a motor drive circuit 61, and by the output from the motor drive circuit 61, a motor 62 may move the measuring portion 1 in the forward and rearward direction relative to the eye E to be examined through a male screw 64 mounted on a table 63. On the table 63, there is also provided a rotation preventing member 65 for preventing the male screw 64 from being rotated by the motor 62 to thereby rotate the measuring portion 1. Further, when a moving member 66 formed with a female thread corresponding to the male screw 64 and formed with a hole corresponding to the rotation preventing member 65 is moved, the convex portion 67a of a switch 67 provided on the tip end of the moving member 66 is adapted to be pushed by switch pushing members 68 and 69, and the output of the switch 67 is connected to the arithmetic processing control circuit 46.

Also, as a similar construction for moving the measuring portion 1 in the vertical direction relative to the eye E to be examined, the output of the arithmetic processing control circuit 46 is connected to a motor drive circuit 70, and by the output from the motor drive circuit 70, a motor 71 may move the measuring portion 1 in the vertical direction relative to the eye E to be examined, through a male screw 73 mounted on a table 72. On the table 72, there is also provided a rotation preventing member 74 for preventing the male screw 73 from being rotated by the motor 71 to thereby rotate the measuring portion 1. Further, when a moving member 75 formed with a female thread corresponding to the male screw 73 and formed with a hole corresponding to the rotation preventing member 74 is moved, the convex portion 76a of a switch 76 provided on the fore end of the moving member 75 is adapted to be pushed by switch pushing members 77 and 78, and the output of the switch 76 is connected to the arithmetic processing control circuit 46.

Further, as a similar construction for moving the measuring portion 1 in the horizontal direction relative to the eye E to be examined, the output of the arithmetic processing control circuit 46 is connected to a motor drive circuit 79, and by the output from the motor drive circuit 79, a motor 80 may move the measuring portion 1 in the leftward and rightward direction relative to the eye E to be examined, through a male screw 82 mounted on a table 81. On the table 81, there is also provided a rotation preventing member 83 for preventing the male screw 82 from being rotated by the motor 80 to thereby rotate the measuring portion 1. When a moving member 84 formed with a female thread corresponding to the male screw 82 and formed with a hole corresponding to the rotation preventing member 83 is moved, the convex portion 85a of a switch 85 provided on the fore end of the moving member 84 is adapted to be pushed by pushing members 86 and 87, and the output of the switch 85 is connected to the arithmetic processing control circuit 46.

The output of the arithmetic processing control circuit 46 is connected to a motor 89 through a motor drive circuit 88 so as to rotate a male screw 90 by the motor 90. A support post 91 internally formed with a female thread corresponding to the male screw 90 is mounted on the male screw 90, and the chin rest 3 mounted on this support post 91 may be vertically moved by electric driving to bring the position of the eye E to be examined to a level substantially capable of effecting an eye examination. The support post 91 is supported by a support post receiver 92 provided with a key way 92a, and by this key way 92a and a key 93 mounted on the support post receiver 92, the chin rest 3 is prevented from being rotated even if the motor 89 is rotated to thereby rotate the male screw 90, and the range of movement of the chin rest 3 is thus controlled.

Further, the output of the arithmetic processing control circuit 46 is connected to the printer 5 shown in FIG. 1 through a printer control circuit 94 and on the other hand, the outputs of the print switch 8, a power source detection circuit 95 to which the power source switch 9 is connected, the chin rest raising switch 10, the chin rest lowering switch 11, the eye examination switch 12 and the sleep switch 13 are connected to the arithmetic processing control circuit 46. Further, the track ball 7 shown in FIG. 1 is connected. to the arithmetic processing control circuit 46 through a track ball signal processing circuit 96. A rotary encoder 98 for detecting the direction and amount of rotation of the roller 6 is connected to the roller 6 through a belt 97, and the output of this rotary encoder 98 is connected to the arithmetic processing control circuit 46 through a rotary encoder signal processing circuit 99 for processing a signal from the rotary encoder 98.

Also, the arithmetic processing control circuit 46 has connected thereto a battery 100 capable of charging electric power as long as the power source is switched on, and using the charge electric power as long as the power source is switched off, a power source circuit 101 for enabling this apparatus to use the electric power received from the outside, and a time measuring circuit 102 for measuring time, and further the output of the arithmetic processing control circuit 46 is connected to the liquid-crystal monitor 4 shown in FIG. 1 through a display signal processing circuit 103.

During an eye examination, the level of the chin rest 3 is adjusted by the chin rest raising switch 10 and the chin rest lowering switch 11 so that the eye E to be examined may become near the nozzle 27 in conformity with the size of the head of the examinee S, and the brow and chin of the examinee S are fixed by a brow applying portion, not shown, and the chin rest 3, respectively. When at this time, the chin rest raising switch 10 or the chin rest lowering switch 11 is depressed, the signal thereof is outputted to the arithmetic processing control circuit 46, from which a drive signal is thus outputted to the motor 89 through the motor drive circuit 88 to thereby raise or lower the chin rest 3.

A light beam from the fixation lamp 39 passes through the lens 38, is reflected by the light dividing member 30, passes through the light passing member 29, the light dividing member 26 and the opening portion of the apertured light passing member 28, and is projected onto the fundus Eγ of the eye E to be examined. The examinee S fixates at this light beam from the fixation lamp 39, whereby the visual axis of the eye E to be examined is fixed.

A light beam from the light source 21 for eye examination passes through the aperture 22, the lens 23 and the light passing member 25, is reflected by the light dividing member 26, passes through the opening portion of the apertured light passing member 28 and is projected onto the cornea Ec. The reflected light beam from the cornea Ec returns along the same optical path, passes through the light dividing member 26, the light passing member 29, the light dividing member 30, the lens 31, the light dividing member 32, the lens 33, the light dividing member 34 and the aperture 35 and is received by the light receiving element 36. The light reception signal of this light receiving element 36 is outputted to the arithmetic processing control circuit 46 through the alignment detection circuit 37, and how accurately right the alignment is is displayed on the light crystal monitor 4 through the display signal processing circuit 103.

Also, the reflected light beam from the front eye part by the light beam from the light source 21 for eye examination passes through the lens 40 and enters the TV camera 41, and the reception signal of this TV camera 41 is outputted to the arithmetic processing control circuit 46 through the image signal processing circuit 42, and a front eye part image Pf is displayed on the liquid-crystal monitor 4 through the display signal processing circuit 103. Also, the cornea reflected light beam by the light beam from the light source 21 for eye examination is reflected by the light dividing member 34, passes through the aperture 43 and enters the light receiving element 44, and the predetermined deformation of the cornea Ec is detected.

An examiner moves the measuring portion 1 in three-dimensional direction, i.e., the forward and rearward direction, the vertical direction and the leftward and rightward direction, relative to the eye E to be examined, by the use of the roller 6 and the track ball 7 while watching the liquid-crystal monitor 4, to thereby effect alignment in such a manner that the quantity of light on the light receiving element 36 becomes maximum.

When as a method of operating the roller 6 and the track ball 7 for actually effecting alignment, the roller 6 is rotated toward the examinee S, the rotation thereof is outputted to the rotary encoder 98 through the belt 97, and a signal conforming to the rotation is outputted from the rotary encoder 98 to the rotary encoder signal processing circuit 99 and the arithmetic processing control circuit 46. The arithmetic processing control circuit 46 controls the motor drive circuit 61 to thereby rotate the motor 62 and move the measuring portion 1 toward the eye E to be examined. Likewise, when the roller 6 is rotated in a direction opposite from the examinee S, the measuring portion 1 is moved away from the eye E to be examined. In this manner, the measuring portion 1 is moved in the forward and rearward direction relative to the examinee S, whereby the eye E to be examined is focused.

Here, the range of movement of the measuring portion 1 when moved in the forward and rearward direction relative to the examinee S is prescribed by the switch 67 and the switch pushing members 68 and 69, and when the measuring portion 1 is moved toward the examinee S and the convex portion 67*a* of the switch 67 is pushed by the switch pushing member 68, the signal from the switch 67 is outputted to the arithmetic processing control circuit 46, which thus controls the motor drive circuit 61 to stop the driving of the motor 62, whereby the measuring portion 1 is stopped. Likewise, when the measuring portion 1 is moved away from the examinee S and the convex portion 67*a* is pushed by the switch pushing member 69, the driving of the motor 62 is stopped, whereby the measuring portion 1 is stopped. The arithmetic processing control circuit 46 memorizes in which direction the measuring portion 1 has so far been moved, and when the measuring portion 1 is to be moved next, it is moved in a direction opposite to the direction in which it has been moved before the convex portion 67*a* is pushed.

When in consequence to the roller 6, the track ball 7 is rotated toward the examinee S, the signal thereof is outputted to the track ball signal processing circuit 96 and the arithmetic processing control circuit 46, which thus controls the motor drive circuit 70 to rotate the motor 71 and thereby move the measuring portion 1 upwardly relative to the eye E to be examined. At this time, the measuring portion 1 is moved upwardly relative to the eye E to be examined and therefore, the front eye part image Pf in the liquid-crystal monitor 4 moves downwardly. Likewise, when the track ball 7 is rotated in a direction opposite from the examinee S, the measuring portion 1 is moved downwardly relative to the eye E to be examined and therefore, the front eye part image Pf in the liquid-crystal monitor 4 moves upwardly.

The range of movement of the measuring portion 1 when moved in the vertical direction relative to the examinee S is prescribed by the switch 76 and the switch pushing members 77 and 78, and when the convex portion 76*a* of the switch 76 is pushed by the switch pushing members 77 and 78, the motor drive circuit 70 is controlled to stop the motor 71, whereby the measuring portion 1 is stopped. When the measuring portion 1 is to be moved next, it is moved in a direction opposite to the direction in which it has been moved before the convex portion 76*a* is pushed.

Also, when the track ball 7 is rotated leftwardly relative to the examinee S, the signal thereof is outputted to the track ball signal processing circuit 96 and the arithmetic processing control circuit 46, which thus controls the motor drive circuit 79 to rotate the motor 80 and thereby move the measuring portion 1 leftwardly relative to the eye E to be examined. At this time, the measuring portion 1 is moved leftwardly relative to the eye E to be examined and therefore, the front eye part image Pf in the liquid-crystal monitor 4 moves rightwardly. Likewise, when the track ball 7 is rotated rightwardly relative to the examinee S, the measuring portion 1 is moved rightwardly relative to the eye E to be examined and therefore, the front eye part image Pf in the liquid-crystal monitor 4 moves leftwardly.

The movement of range of the measuring portion 1 when moved in the leftward and rightward direction relative to the examinee S is prescribed by the switch 85 and the switch pushing members 86 and 87, and when the convex portion 85*a* of the switch 85 is pushed by the switch pushing members 86 and 87, the motor drive circuit 79 is controlled to stop the motor 80, whereby the measuring portion 1 is stopped. When the measuring portion 1 is to be moved next, it is moved in a direction opposite to the direction in which it has been moved before the convex portion 85*a* is pushed.

When the eye examination switch 12 is depressed after the measuring portion 1 has thus been moved in the forward and rearward direction, the vertical direction and the leftward and rightward direction relative to the eye E to be examined to thereby effect alignment, an eye examination begins. When the eye examination switch 12 is depressed, an eye examination starting signal is outputted from the eye examination switch 12 to the arithmetic processing control circuit 46, from which a drive signal is thus outputted to the rotary solenoid drive circuit 47 and the rotary solenoid 48 to thereby rotate the rotary solenoid rightwardly as viewed in FIG. 2.

When the rotary solenoid 48 is rightwardly rotated, the piston 51 rises along the cylinder 52 through the link mechanisms 49 and 50 and thus, the pressure in the chamber 24 heightens and air is blown from the nozzle 27 toward the cornea Ec. The cornea Ec against which the air has been blown is pushed and gradually makes predetermined deformation, which is detected by the light receiving element 44, and the signal from this light receiving element 44 is outputted to the arithmetic processing control circuit 46 through the predetermined deformation detection circuit 45.

Also, the pressure value in the chamber 24 when the cornea Ec has made the predetermined deformation can be converted into an intra ocular pressure value, and the calculation of the conversion thereof into the intra ocular pressure value is effected in the arithmetic processing control circuit 46 in accordance with a conversion table found by an experiment or the like. When the intra ocular pressure value has been found in the arithmetic processing control circuit 46, the intra ocular pressure value is displayed on the liquid-crystal monitor 4. Instead of depressing the eye examination switch 12 to thereby effect measurement after alignment has been done, if an automatic measuring function is given to the apparatus, design may be made such that an eye examination is automatically effected when alignment is done.

Figure 4:
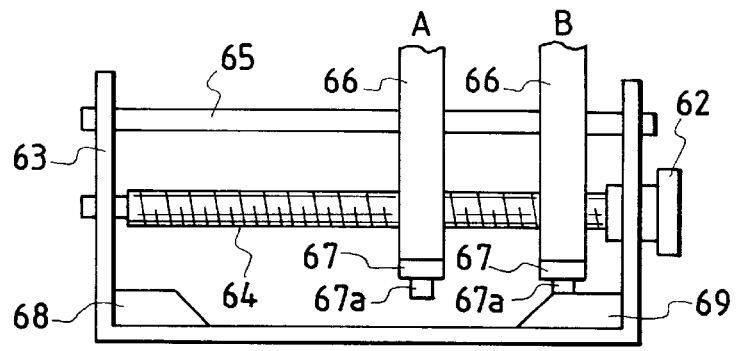
FIG. 4 is an illustration of the positional relation of a moving member.

Also, when the apparatus is left unused for a while after the termination of the eye examination, the examiner operates the sleep switch 13, whereby the measuring portion 1 is moved to a predetermined position in an eye examination waiting state. FIG. 4 is an illustration showing the positional relation of the moving member 66. When the sleep switch 13 is depressed, the signal thereof is outputted to the arithmetic processing control circuit 46, which thus controls the motor drive circuit 61 to drive the motor 62 and thereby move the moving member 66 from a position A toward a position B. When the convex portion 67*a* of the switch 67 is pushed by the switch pushing member 69 at the position B, a stop signal is outputted from the switch 67 to the arithmetic processing control circuit 46, which thus controls the motor drive circuit 61 to stop the motor 62, whereby the moving member 66 is stopped at the position B.

Figure 5:
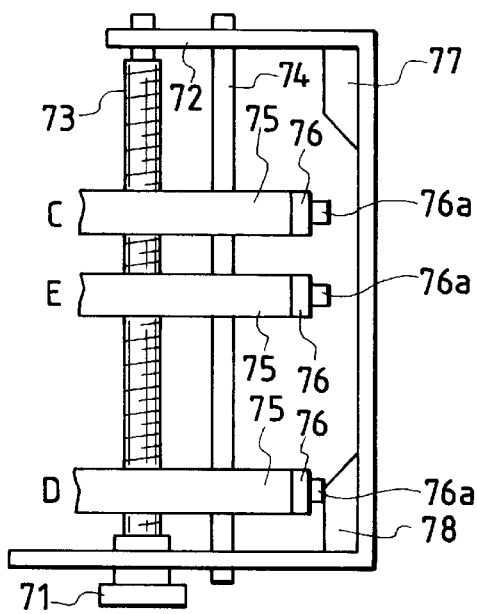
FIG. 5 is an illustration of the positional relation of the moving member.

FIG. 5 is an illustration showing the positional relation of the moving member 75. When the sleep switch 13 is depressed, the arithmetic processing control circuit 46 controls the motor drive circuit 70 to drive the motor 71 and thereby move the moving member 75 from a position C toward a position D. When the convex portion 76a of the switch 76 is pushed by the switch pushing member 78 at the position D, a stop signal is outputted from the switch 76 to the arithmetic processing control circuit 46, which thus controls the motor drive circuit 70 to stop the motor 71, whereby the moving member 75 is stopped at the position D. Subsequently, the arithmetic processing control circuit 46 controls the motor drive circuit 70 to drive the motor 71 and thereby move the moving member 75 from the position D to a position E immediate of the switch pushing members 77 and 78.

Here, how many times the male screw 73 should be rotated to move the moving member 75 from the position D to the position E is found in advance by an experiment, a calculation or the like, and the male screw 73 is rotated the found predetermined times, whereby the moving member 75 can be moved from the position D to the position E. Instead of the moving member 75 being moved from the position D in which the convex portion 76a is pushed by the switch pushing member 78 to the position E, design may be made such that the moving member is moved from a position in which the convex portion 76a is pushed by the switch pushing member 77 to the position e.

Figure 6:
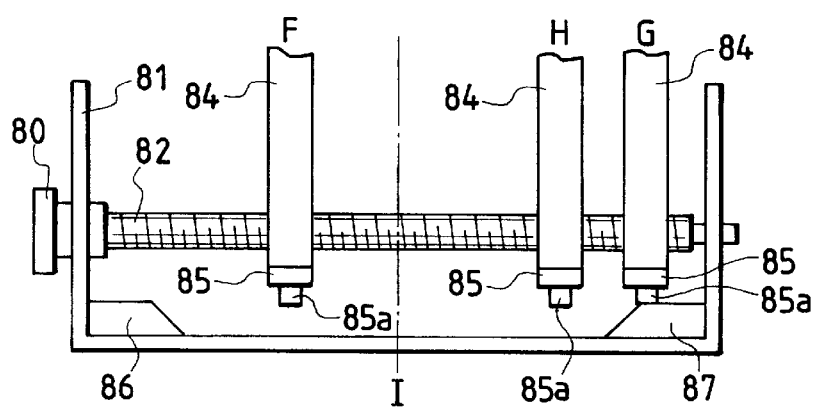
FIG. 6 is an illustration of the positional relation of the moving member.

FIG. 6 is an illustration showing the positional relation of the moving member 84 as it is seen from the direction of the examinee S. When the sleep switch 13 is depressed, the arithmetic processing control circuit 46 controls the motor drive circuit 79 to drive the motor 80 and thereby move the moving member 84 from a position F toward a position G. When the convex portion 85a of the switch 85 is pushed by the switch pushing member 87 at the position G, a stop signal is outputted from the switch 85 to the arithmetic processing control circuit 46, which thus controls the motor drive circuit 79 to stop the motor 80, whereby the moving member 84 is stopped at the position G. Subsequently, the arithmetic processing control circuit 46 controls the motor drive circuit 79 to drive the motor 80 and thereby moving the moving member 84 from the position G to a position H.

This position H is a position which is more toward the right eye by ½ of the distance between an average person's left and right eyes than a position I intermediate of the switch pushing members 86 and 87. Also, regarding the movement from the position G to the position H, as in the case of the movement from the position D to the position E shown in FIG. 5, how many times the male screw 82 should be rotated is found in advance. Instead of the moving member being from the position G in which the convex portion 85a is pushed by the switch pushing member 87 to the position H, design may be made such that the moving member is moved from a position in which the convex portion 85a is pushed by the switch pushing member 86 to the position H, or instead of the moving member being moved to the position H of the right eye, design may be made such that the moving member is moved to the position of the left eye.

Further, design is made such that when the sleep switch 13 is depressed and the measuring portion 1 is moved to a predetermined position, it is sequentially moved in each one direction of three directions, whereas the movement of the measuring portion 1 is not restricted to each one direction, but design may be made such that the measuring portion is moved in three directions at a time or moved in one direction before and after it is moved in two directions at a time.

Also, the supply of electric power to the liquid-crystal monitor 4, the light source 21 for eye examination, the fixation lamp 39, etc. can be stopped by depressing the sleep switch 13 in order to save the electric power and extend the service life of each member. For this purpose, design can be made such that when the sleep switch 13 is depressed, the signal thereof is outputted to the arithmetic processing control circuit 46 to thereby stop the supply of the electric power to the liquid-crystal monitor 4, the light source 21 for eye examination and the fixation lamp 39.

Even if the sleep switch 13 is not especially provided, to move the measuring portion 1 to the predetermined position in the eye examination waiting state, design may be made such that the print switch 8, the chin rest raising switch 10, the chin rest lowering switch 11, etc. are operated after the termination of the eye examination, whereby the measuring portion 1 is moved to the predetermined position. For example, when the print switch 8 is operated, the signal thereof is outputted from the arithmetic processing control circuit 46 to the printer control circuit 94 and data such as the results of the eye examination of the left and right eyes, the frequency of the eye examination, the date and time of the eye examination, the name of the examinee S and ID number are printed out from the printer 5 onto paper P. After the data have been printed out, the measuring portion 1 is moved to the predetermined position.

Also, when the input means such as the roller 6, the track ball 7, the print switch 8, the chin rest raising switch 10, the chin rest lowering switch 11, the eye examination switch 12 and the sleep switch 13 are left unoperated, the fact that these input means are not operated is detected by the arithmetic processing control circuit 46 and the time for which these input means are not operated is measured by the time measuring circuit 102.

When these input means are left unoperated for a predetermined time such as five minutes, ten minutes or the like, a signal is outputted from the time measuring circuit 102 to the arithmetic processing control circuit 46, whereby the measuring portion 1 is moved to the predetermined position and at the same time, the supply of the electric power to the liquid-crystal monitor 4, the light source 21 for eye examination, the fixation lamp 39, etc. is stopped to save the electric power and extend the service life of each member.

Further, design can also be made such that time is measured by the time measuring circuit 102 and when the time has become, for example, 8:30 a.m., the measuring portion 1 is moved to the predetermined position and the supply of the electric power to the liquid-crystal monitor 4, the light source 21 for eye examination, the fixation lamp 39, etc. is effected so that an eye examination can be made. Likewise, when the time has become a predetermined time such as 5:45 p.m., the measuring portion 1 is moved to the predetermined position and the supply of the electric power to the liquid-crystal monitor 4, the light source 21 for eye examination, the fixation lamp 39, etc. is stopped.

Also, when the power source switch 9 has been operated to switch on the power source, the power source detection circuit 95 outputs to the arithmetic processing control circuit 46 the fact that the power source has been switched on, and the power source of the electric system is connected to the power source circuit 101 by the arithmetic processing circuit 46, whereby the battery 100 is charged and the measuring portion 1 is moved to the predetermined position.

Also, when the power source switch 9 has been operated to switch off the power source, the power source detection circuit 95 outputs to the arithmetic processing control circuit 46 the fact that the power source has been switched off, and the arithmetic processing control circuit 46 changes the power source from a power source using the usual electric power when the power source is separated from the power source circuit 101 and is connected to the battery 100 for the supply of the electric power to a power source using electric power charged by the battery 100. The electric power from this battery 100 is supplied to the arithmetic processing control circuit 46, the motor drive circuits 61, 70, 79, the motors 62, 71, 80, the switches 67, 76, 85, etc. to thereby move the measuring portion 1 to the predetermined position.

As described above, the time has become the predetermined time, the operating means is not operated for a predetermined time, the input means is operated after the termination of the eye examination or the power source is switched on and off, whereby the drive means for moving the measuring portion 1 to the predetermined position and the means for effecting the alignment of the eye E to be examined and the apparatus are provided by a single means and thus, the cost can be made low. Also, during the time for which the eye examination of an examinee is terminated and the eye examination of the next examinee is made, the measuring portion 1 can be moved to the predetermined position and therefore, the possibility of the fore end of the measuring portion 1 striking against the next examinee's eye to be examined becomes small and stability is improved. Further, it is possible to start the next eye examination from the predetermined position which is always near the left eye or the right eye and therefore, the next eye examination can be done quickly and operability is good.

Figure 7:
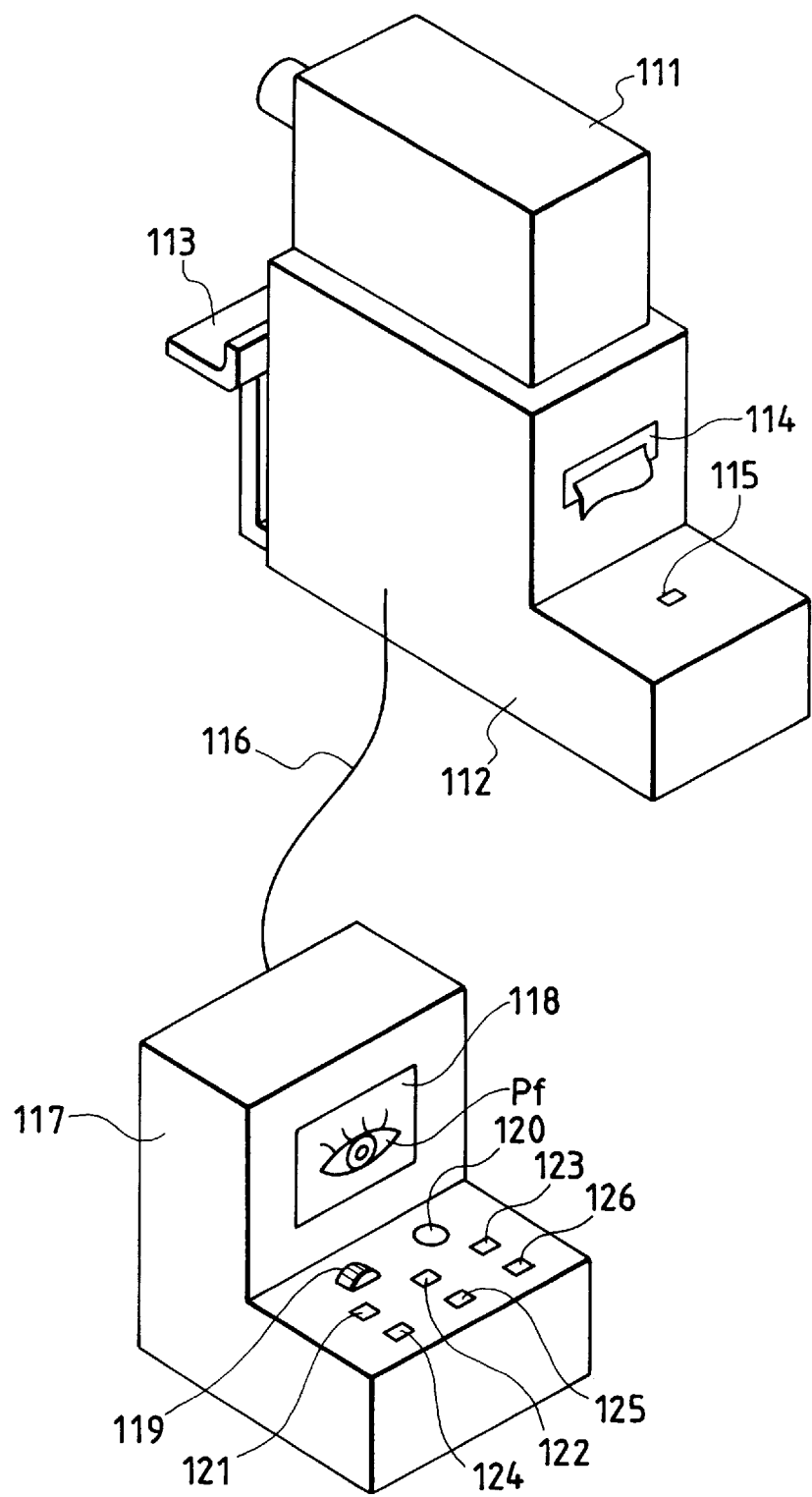
FIG. 7 is a perspective view of a second embodiment of the present invention.

FIG. 7 is a perspective view of an apparatus according to a second embodiment of the present invention. In this embodiment, a measuring portion 111 for effecting an eye examination is substantially similar to the measuring portion 1 in the first embodiment shown in FIG. 2, and the measuring portion 111 is movably placed on a fixed base 112, on which there are provided a chin rest 113 for fixing the position of the examinee's head and movable in a vertical direction, a printer 114 and a power source switch 115 for switching on and off a power source. Also, an operating body 117 is connected to the fixed base 112 through a cord 116. On this operating body 117, there are provided a liquid-crystal monitor 118, a roller 119, a track ball 120, a print switch 121, a chin rest raising switch 122, a chin rest lowering switch 123, an eye examination switch 124, a sleep switch 125 and a predetermined position changing switch 126, and unlike the first embodiment, these mechanisms are not provided on the fixed base 112.

Design is made such that by rotating the roller 119 the measuring portion 111 is one-dimensionally aligned with the eye E to be examined, and by rotating a ball in the track ball 120, the eye E to be examined is two-dimensionally aligned. Also, when the sleep switch 125 has been operated, or when operating means such as the roller 119, the track ball 120, the chin rest raising switch 122, the chin rest lowering switch 123 and the eye examination switch 124 have not been operated even after a predetermined time has elapsed, or when the power source has been turned on and off, the measuring portion 111 is moved to a predetermined position, and design is made such that the predetermined position can be changed by the predetermined position changing switch 126.

Figure 8:
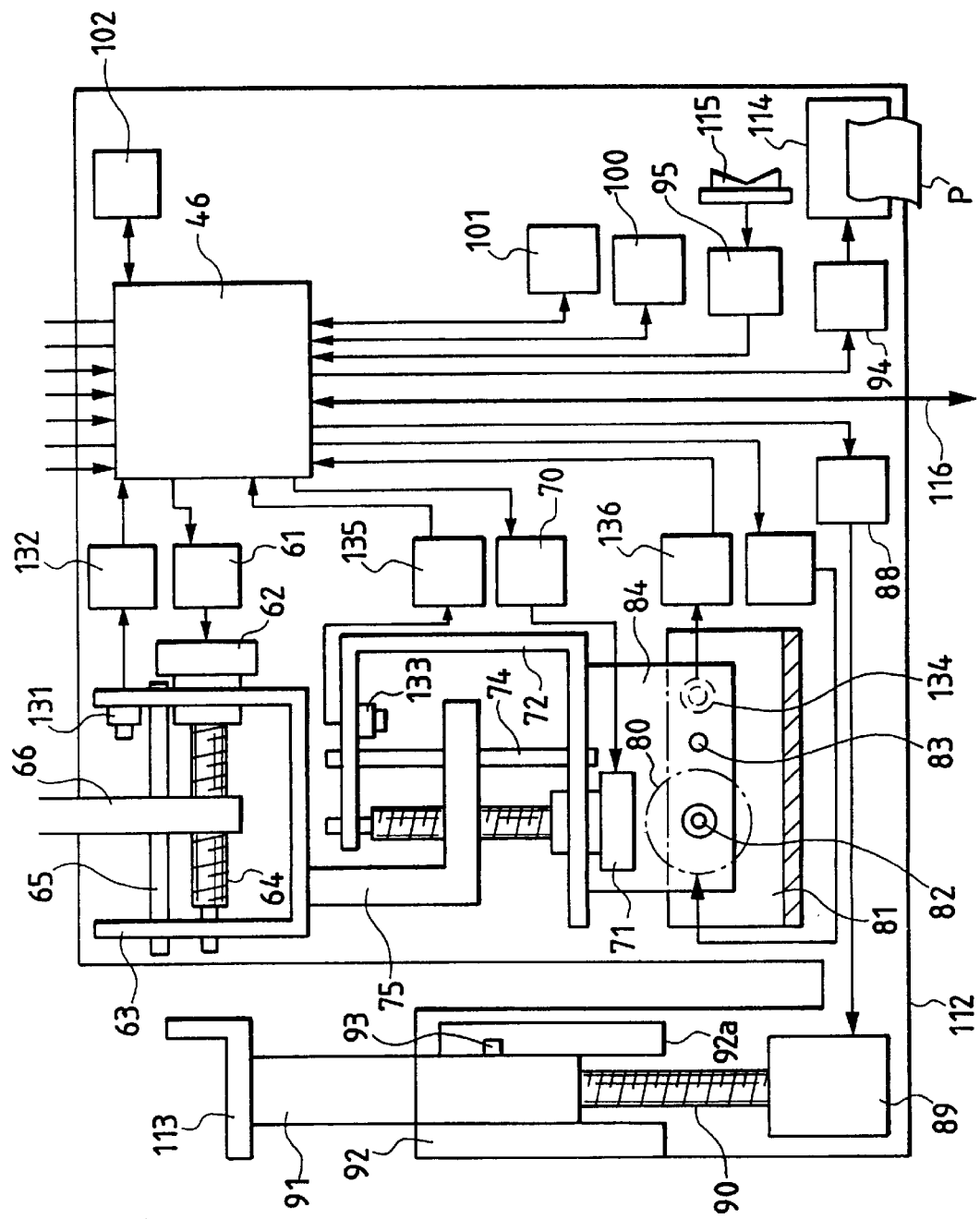
FIG. 8 is a block circuit diagram of the interior of a fixed base.

FIG. 8 is a block circuit diagram of the interior of the fixed base 112, and in FIG. 8, the same reference numerals as those in FIG. 3 designates the same members. In FIG. 8, a distance sensor 131 is provided on the table 63 so that by detecting the distance to the moving member 66, the position of the measuring portion 111 in the forward and rearward direction when seen from the examinee S may be confirmed. The output of this distance sensor 131 is connected to the arithmetic processing control circuit 46 through a distance detection circuit 132 for finding the distance, and the switch 67 and the switch pushing members 68 and 69 shown in FIG. 3 are not provided.

Likewise, on the tables 72 and 81, there are provided distance sensors 133 and 134, respectively, for confirming the positions of the measuring portion 111 in the vertical direction and horizontal direction when seen from the examinee S, and these distance sensors 133 and 134 are connected to the arithmetic processing control circuit 46 through distance detection circuits 135 and 136, respectively.

The switches 76, 85 and the switch pushing members 77, 78, 86, 87 shown in FIG. 3 are neither provided. Further, on the fixed base 112, there are not provided the liquid-crystal monitor 4, the roller 6, the track ball 7, the print switch 8, the chin rest raising switch 10, the chin rest lowering switch 11, the eye examination switch 12, the sleep switch 13, the track ball signal processing circuit 96, the belt 97, the rotary encoder 98, the rotary encoder signal processing circuit 99 and the display signal processing circuit 103.

Figure 9:
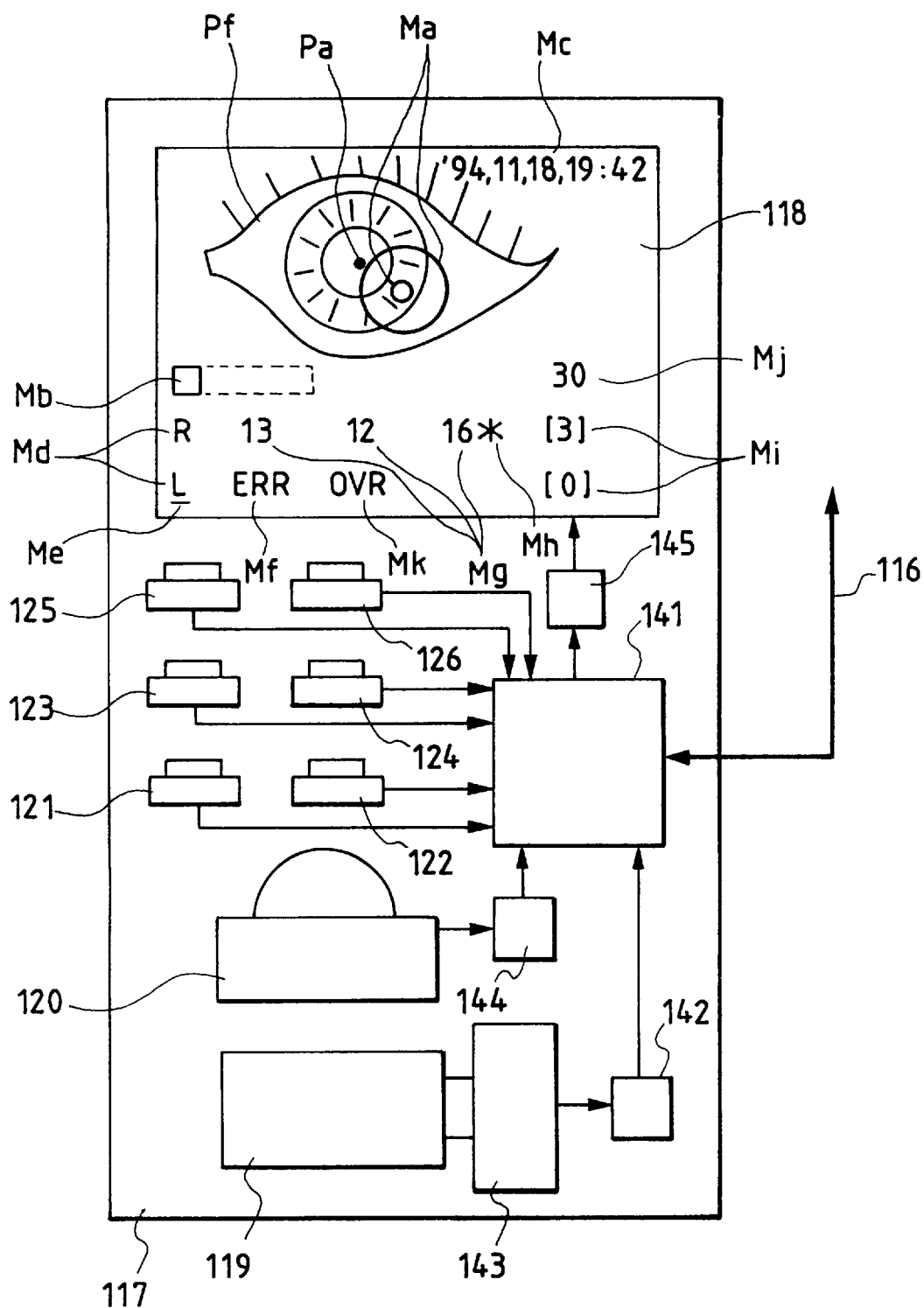
FIG. 9 is a block circuit diagram of the interior of an operating body.

Referring now to FIG. 9 which is a block circuit diagram of the operating body 117, the input and output of the arithmetic processing control circuit 46 in the fixed base 112 are connected to an arithmetic processing control circuit 141 through the cord 116. A rotary encoder processing circuit 142 and a rotary encoder 143 for detecting the direction and amount of rotation of the roller 119 are successively connected to the input of the arithmetic processing control circuit 141, and the roller 119 is mounted on the rotary encoder 143. Further, a track ball signal processing circuit 144 for processing the signal from the track ball 120, and the track ball 120 are successively connected to the input of the arithmetic processing control circuit 141.

Also, the print switch 121, the chin rest raising switch 122, the chin rest lowering switch 123, the eye examination switch 124, the sleep switch 125 and the predetermined position changing switch 126 are connected to the input of the arithmetic processing control circuit 141. The output of the arithmetic processing control circuit 141 is connected to the liquid-crystal monitor 118 through a display signal processing circuit 145.

During an eye examination, the head of the examinee S is fixed and the examinee S is made to fixate at the fixation lamp 39, whereby the visual axis of the eye E to be examined is fixed. The front eye part image Pf received by the TV camera 41 is outputted to the arithmetic processing control circuit 46 through the image signal processing circuit 42, and is further outputted to the arithmetic processing control circuit 141 through the cord 116, and the front eye part image Pf is displayed from the display signal processing circuit 145 onto the liquid-crystal monitor 118.

On the liquid-crystal monitor 118, there are displayed the front eye part image Pf, an alignment luminescent spot image Pa which indicates the position of the light beam from the light source 21 for eye examination and from which the deviation between the positions of the measuring portion 111 and the eye E to be examined can be known, an alignment mark Ma for alignment detection, and a level meter mark Mb indicative of the quantity of light on the light receiving element 36 to display the accuracy of alignment position more finely.

On the liquid-crystal monitor 118, there are further displayed a clock display mark Mc indicative of the date and time of measurement, a left-and-right-eye display mark Md indicative of the left and right eyes, a displayed eye mark Me indicating which of the left and right eyes the front eye part image Pf being displayed on the liquid-crystal monitor 118 is, an error mark Mf indicative of the measurement being impossible, an intra ocular pressure value mark Mg indicative of the intra ocular pressure value, a low reliability mark Mh indicative of the fact that the reliability of the intra ocular pressure value due to alignment position deviation is low, a measurement frequency mark Mi, a measurement range value mark Mj indicative of the measurement range of the intra ocular pressure, and a measurement range value over display mark Mk displayed when the measurement range value mark Mj is exceeded.

Figure 10:
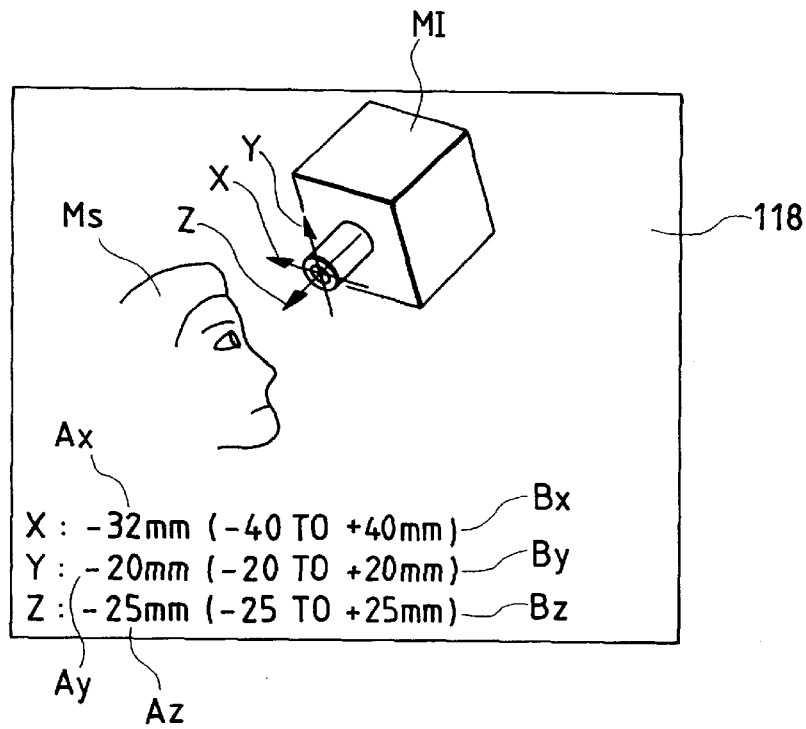
FIG. 10 is an illustration of the display screen of a liquid-crystal monitor during a mode for changing a predetermined position.

FIG. 10 shows the display screen of the liquid-crystal monitor 118 when the predetermined position changing switch 126 has been operated. On the liquid-crystal monitor 118, there are displayed an examinee mark Ms which is a picture reproducing the examinee, a measuring portion mark Ml which is a picture reproducing the measuring portion 111 opposed to the examinee mark Ms, and coordinates X, Y and Z indicative of the coordinates of the measuring portion 111 in the leftward and rightward direction, the vertical direction and the forward and rearward direction as viewed from the examinee S. Further, in the lower portion of the liquid-crystal monitor 118, there are displayed movement positions Ax, Ay and Az indicative of the respective positions in the directions of the coordinates X, Y and Z when the measuring portion 111 is moved to the predetermined position, and movement ranges Bx, By and Bz in the unit of mm indicative of the values of the movement ranges of the measuring portion 111 in the directions of the coordinates X, Y and Z.

The intersection point of the coordinates Y and the coordinates Z is defined as zero, and the movement position Ax and the movement range Bx are displayed so that the left eye side as viewed from the eye E to be examined may be positive and the right eye side as viewed from the eye E to be examined may be negative. Likewise, the point of intersection between the coordinates Z and the coordinates X is defined zero, and the movement position Ay and the movement range By are displayed so that the upper side as viewed from the eye E to be examined may be positive and the lower side as viewed from the eye E to be examined may be negative, and the point of intersection between the coordinates X and the coordinates Y is defined as zero, and the movement position Az and the movement range Bz are displayed so that the direction toward the eye E to be examined as viewed from the eye E to be examined may be positive and the direction away from the eye E to be examined as viewed from the eye E to be examined may be negative.

Also, design is made such that the position of the measuring portion 111 when the coordinates X are 0 mm becomes substantially equal to the central position between the left and right eyes of the examinee S when the head of the examinee S is prescribed by the chin rest 113 or the like, and becomes the center of the range within which the measuring portion 111 can be moved in the direction of the coordinates X. Likewise, the position of the measuring portion 111 when the coordinates Y are 0 mm is the center of the range within which the measuring portion 111 can be moved in the direction of the coordinates Y, and the position of the measuring portion 111 when the coordinates Z are 0 mm is the center of the range within which the measuring portion 111 can be moved in the direction of the coordinates Z.

While watching the liquid-crystal monitor 118, the examiner adjust the alignment of the measuring portion 111 in the vertical direction and the leftward and the rightward direction relative to the examinee S by the use of the track ball 120 in such a manner that the alignment luminescent spot image Pa coincides with the center of the alignment mark Ma, and adjusts the alignment of the measuring portion 111 in the forward and rearward direction relative to the examinee S by the use of the roller 119 in such a manner that the level meter mark Mb becomes a maximum level. After by thus operating the roller 119 and the track ball 120, the examiner has adjusted the alignment in the forward and rearward direction, the vertical direction and the leftward and rightward direction relative to the eye E to be examined as in the first embodiment, the examiner depresses the eye examination switch 124, whereupon an eye examination begins. When the intra ocular pressure value has been found, the intra ocular pressure value mark Mg is displayed on the liquid-crystal monitor 118, and in some cases, the error mark Mf, the low reliability mark Mh and the measurement range value over display mark Mk are displayed.

Also, as in the first embodiment, the time has become a predetermined time, the predetermined time operating means has not been operated, the input means such as the print switch 121 and the sleep switch 125 have been operated after the termination of the eye examination, or the power source is switched on and off, whereby the measuring portion 111 is moved to a predetermined position. This movement to the predetermined position is effected by the distances to the moving members 66, 75 and 84 being measured by the distance sensors 131, 133 and 134, respectively, and being outputted from the distance detection circuits 132, 135 and 136 to the arithmetic processing control circuit 46 to thereby drive the motors 62, 71 and 80. This predetermined position is the movement positions Ax, Ay and Az shown in FIG. 10, and in this case, the measuring portion 111 is moved to a position in which the value of the coordinates X is −32 mm, the value of coordinates Y is −20 mm and the value of the coordinates Z is −25 mm.

Also, when the predetermined position should be changed, the predetermined position changing switch 126 is operated to thereby bring the display screen of the liquid-crystal monitor 118 into a mode for changing the predetermined position shown in FIG. 10. In this mode, in the same manner as when alignment is effected, the roller 119 and the track ball 120 are operated to thereby change the values of the movement positions Ax, Ay and Az, and a new predetermined position is memorized by the arithmetic processing control circuit 46.

Figure 11:
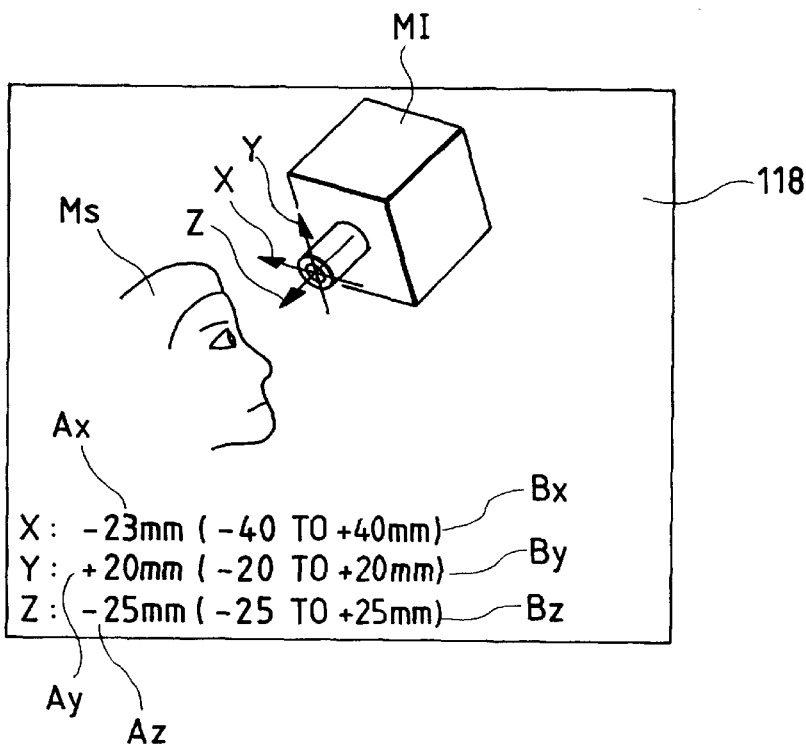
FIG. 11 is an illustration of the display screen of the liquid-crystal monitor when the predetermined position has been changed.

FIG. 11 is an illustration of the display screen of the liquid-crystal monitor 118 after the values of the movement positions Ax, Ay and Az have been changed, and as compared with FIG. 10, the movement position Ax is changed from −32 mm to −23 mm, the movement position Ay is changed from −20 mm to +20 mm, and the movement position Az is not changed. When the measuring portion 111 is to be moved to the predetermined position after these changes have been effected, the measuring portion 111 is moved to this newly changed predetermined position.

Instead of the examiner freely changing the predetermined position within the range in which the movement of the measuring portion 111 is possible, several predetermined positions of the measuring portion 111 can be prepared in advance and the examiner can select one from among them and change the predetermined position to a predetermined position the examiner likes. For example, the first predetermined position is one in which the value of the coordinates X is −32 mm, the value of the coordinates Y is −20 mm and the value of the coordinates Z is −25 mm, the second predetermined position is one in which the value of the coordinates X is +32 mm, the value of the coordinates Y is −20 mm and the value of the coordinates Z is −25 mm, the third predetermined position is one in which the value of the coordinates X is −32 mm, the value of the coordinates Y is +20 mm and the value of the coordinates Z is −25 mm, and the fourth predetermined position is one in which the value of the coordinates X is +32 mm, the value of the coordinates Y is +20 mm and the value of the coordinates Z is −25 mm.

By thus preparing four kinds of predetermined positions of the measuring portion 111, and operating the predetermined position changing switch 126, there is brought about the mode for changing the predetermined position, and those four kinds of predetermined positions are displayed on the liquid-crystal monitor 118. When one of these four kinds of predetermined positions is selected, the predetermined position changing switch 126 is again operated, whereby the apparatus goes out of the mode for changing the predetermined position to a new predetermined position.

What is claimed is:

1. An ophthalmologic apparatus for executing an eye examination on an eye to be examined, comprising:

an eye examination unit;

an alignment drive system for driving said eye examination unit to thereby execute alignment between said eye examination unit and the eye to be examined;

a time measuring unit; and a control system for causing said alignment drive system to drive said eye examination unit on the basis of output of said time measuring portion so as to return said eye examination unit to an eye examination waiting position.

2. The apparatus according to claim 1, further comprising changing means for changing said eye examination waiting position.

3. The apparatus according to claim 1, wherein by an operational input, to said eye examination unit having not been effected for a predetermined time, said control system causes said alignment drive system to drive said eye examination unit so as to return said eye examination unit to the eye examination waiting position.

4. The apparatus according to claim 3, wherein by the operational input to said eye examination unit having not been effected for the predetermined time, said control system further stops the supply of electric power to said eye examination unit.

5. The apparatus according to claim 1, wherein said eye examination unit effects intra ocular pressure measurement.

6. An ophthalmologic apparatus for executing an eye examination on an eye to be examined, comprising:

an eye examination unit;

a drive system for driving said eye examination unit at least along a direction opposed to the eye to be examined;

an input switch for causing said eye examination unit to execute a predetermined process after termination of the eye examination; and a control system for causing said drive system to drive said eye examination unit in conformity with input of said input switch so as to return said eye examination unit to an eye examination waiting position with respect to at least the direction opposed to the eye to be examined.

7. The apparatus according to claim 6, further comprising changing means for changing said eye examination waiting position.

8. The apparatus according to claim 6, wherein said eye examination unit is capable of printing out the result of the eye examination, and said input switch is a print switch for causing the result of the eye examination to be printed.

9. The apparatus according to claim 6, wherein said eye examination unit has a vertically movable chin rest for fixing an examinee's face, and said input switch is a switch for vertically moving said chin rest.

10. The apparatus according to claim 6, wherein said eye examination unit effects intra ocular pressure measurement.

11. The apparatus according to claim 6, wherein said drive system is capable of driving said eye examination unit also along a direction perpendicular to said opposed direction, and said control system causes said drive system to drive said eye examination unit so as to return said eye examination unit to the eye examination waiting position with respect also to the direction perpendicular to said opposed direction.

12. An ophthalmologic apparatus for executing an eye examination on an eye to be examined, comprising:

an examination unit;

a drive system for driving said eye examination unit; and a control system for causing said drive system to drive said eye examination unit so as to return said eye examination unit to an eye examination waiting position when the supply of electric power to said eye examination unit is cut off.

13. The apparatus according to claim 12, further comprising electric power supply means for supplying said drive system with electric power for returning said eye examination unit to the eye examination waiting position when the supply of electric power to said eye examination unit is cut off.

14. The apparatus according to claim 12, further comprising changing means for changing said eye examination waiting position.

15. The apparatus according to claim 12, wherein said eye examination unit effects intra ocular pressure measurement.

* * * * *

UNITED STATES PATENT AND TRADEMARK OFFICE
CERTIFICATE OF CORRECTION

PATENT NO. : 5,822,034

DATED : October 13, 1998

INVENTOR(S) : SATOSHI SHIMASHITA, ET AL.

It is certified that error appears in the above-identified patent and that said Letters Patent is hereby corrected as shown below:

```
COLUMN 1,
Line 18, "the" should read --the eye of the--.
Line 34, "effects" should read --affects--.
Line 52, "located" should read --located,--.

COLUMN 2,
Line 3, "examinee" should read  --excaminees--.

COLUMN 3,
Line 26, "direction," should read --directions,--.
Line 29, "direction," should read --directions,--.
Line 31, "direction," should read --directions,--.
Line 32, "direction" should read --directions--.

COLUMN 5,
Line 47, "connected." should read --connected--.
Line 61, "101" should read --101 is provided--.
Line 63, "102" should read --102 is provided--.

COLUMN 6,
Line 35, "is" (first occurrence) should read --is,--.
```

UNITED STATES PATENT AND TRADEMARK OFFICE
CERTIFICATE OF CORRECTION

PATENT NO. : 5,822,034

DATED : October 13, 1998

INVENTOR(S) : SATOSHI SHIMASHITA, ET AL.

It is certified that error appears in the above-identified patent and that said Letters Patent is hereby corrected as shown below:

COLUMN 7,
Line 9, "direction" should read --directions--.

COLUMN 8,
Line 11, "direction," (first occurrence) should read --directions,--.
Line 12, "direction" should read --directions--.
Line 33, "intra ocular" should read --intraocular--.
Line 34, "intra ocular" should read --intraocular--.
Line 37, "intra ocular" should read --intraocular--.
Line 39, "intra ocular" should read --intraocular--.

COLUMN 13,
Line 3, "intra ocular" should read --intraocular--.
Line 4, "intra ocular" should read --intraocular--.
Line 5, "intra" should read --intra- --.
Line 9, ""intra ocular" should read --intraocular--.
Line 19, "direction," (first occurrence) should read --directions,--.
Line 20, "direction" should read --directions--.

UNITED STATES PATENT AND TRADEMARK OFFICE
CERTIFICATE OF CORRECTION

PATENT NO. : 5,822,034

DATED : October 13, 1998

INVENTOR(S) : SATOSHI SHIMASHITA, ET AL.

It is certified that error appears in the above-identified patent and that said Letters Patent is hereby corrected as shown below:

COLUMN 13 (Cont.),
Line 36, "defined" should read --defined as--.
Line 67, "tion" should read --tions--.

COLUMN 14,
Line 4, "direction," should read --directions,--.
Line 9, "direction" (first occurrence) should read --directions--.
Line 10, "direction" should read --directions--.
Line 13, "intra ocular" should read --intraocular--.
Line 14, "intra ocular" should read --intraocular--.

COLUMN 15,
Line 19, "eye" should be deleted.
Line 20, "on" should read --of--.
Line 27, "of" should read --of an--.
Line 28, "portion" should read --unit--.
Line 32, "said" should read --the--.
Line 35, "input," should read --input--.
Line 43, "electric" should read --electrical--.
Line 46, "intra ocular" should read --intraocular--.
Line 47, "eye" should be deleted.
Line 48, "on" should read --of--.

UNITED STATES PATENT AND TRADEMARK OFFICE
CERTIFICATE OF CORRECTION

PATENT NO. : 5,822,034

DATED : October 13, 1998

INVENTOR(S) : SATOSHI SHIMASHITA, ET AL.

It is certified that error appears in the above-identified patent and that said Letters Patent is hereby corrected as shown below:

<u>COLUMN 16</u>,
Line 22, "intra ocular" should read --intraocular--.
Line 26, "and" should read --and wherein--.
Line 48, "said" should read --the--.
Line 51, "intra ocular" should read --intraocular--.

Signed and Sealed this

Twenty-eighth Day of September, 1999

Attest:

Q. TODD DICKINSON

*Attesting Officer*     *Acting Commissioner of Patents and Trademarks*